United States Patent [19]

vonBebenburg, deceased et al.

[11] Patent Number: 4,554,281

[45] Date of Patent: Nov. 19, 1985

[54] 2-AMINO-3-ACYLAMINO-6-BENZYLAMINO-PYRIDINE-DERIVATIVE HAVING ANTIEPILEPTIC ACTION

[75] Inventors: Walter vonBebenburg, deceased, late of Dreieich, by Marie vonBebenburg, executrix; Joachim Heese, Hanau; Jurgen Engel, Alzenau, all of Fed. Rep. of Germany; Kurt Thiele, Zofingen, Switzerland

[73] Assignee: Degussa Aktiengesellschaft, Frankfurt, Fed. Rep. of Germany

[21] Appl. No.: 545,930

[22] Filed: Oct. 27, 1983

[30] Foreign Application Priority Data

Oct. 27, 1982 [DE] Fed. Rep. of Germany ....... 3239790

[51] Int. Cl.[4] .................... A61K 31/44; C07D 213/74
[52] U.S. Cl. ..................................... 514/353; 546/308
[58] Field of Search ........................ 424/263; 546/308; 514/353

[56] References Cited

PUBLICATIONS

Richens, A., "Drug Treatment of Epilepsy", Henry Kimpton Publishers, London, (1976) pp. 53-60.

Urca, G. et al, "Morphine and Enkephalin", Chemical Abstracts, 87: 95940q (1977).

Sewell, R. D. E., "Proconvulsant Action of Aspirin", Chemical Abstracts, 99: 151817s (1983).

*Primary Examiner*—Henry R. Jiles
*Assistant Examiner*—Dale A. Bjorkman
*Attorney, Agent, or Firm*—Cushman, Darby & Cushman

[57] ABSTRACT

Compounds of the formula

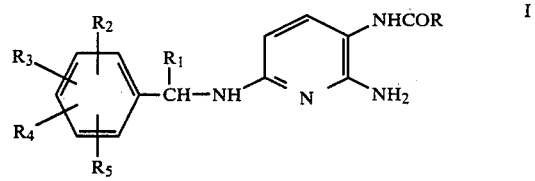

where R is a $C_1$–$C_4$ alkyl group, a $C_1$–$C_4$ alkoxy group, a phenoxy group or a phenyl-$C_1$–$C_2$-alkoxy group, $R_1$ is hydrogen or a $C_1$–$C_4$-alkyl group and $R_5$ is hydrogen or a $C_1$–$C_4$-alkyl group and the groups $R_2$, $R_3$, and $R_4$ are the same or different and are hydrogen, halogen atoms, $C_1$–$C_4$ alkyl groups, $C_1$–$C_4$-alkylcarbonyl group, the aminosulfonyl group, the trifluoromethyl group and their acid addition salts are effective as antiepileptics.

11 Claims, No Drawings

2-AMINO-3-ACYLAMINO-6-BENZYLAMINO-PYRIDINE-DERIVATIVE HAVING ANTIEPILEPTIC ACTION

BACKGROUND OF THE INVENTION

In Belgian Pat. Nos. 698,384 and 764,362 there are disclosed compounds of the following formula:

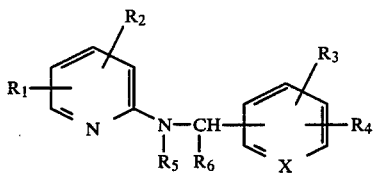

wherein one or more of the groups $R_1$ to $R_4$ are amino groups which can be acylated or alkylated by a low molecular weight group, whereby the remaining groups $R_1$ to $R_4$ which do not represent an amino group are hydrogen or halogen atoms, lower molecular weight alkyl, trifluoromethyl, cyano, thiocyano, mercapto, low molecular weight alkylthio, acylthio, hydroxy, methylenedioxy, low molecular weight alkoxy, acyloxy, nitro, carboxy, carbalkoxy, or carbamoyl groups, $R_5$ is a hydrogen atom or an acyl group, $R_6$ is a hydrogen atom, a low molecular weight alkyl or an aralkyl group and X is a nitrogen atom or the —CH— group and whereby the acyl group is derived from carbonic acid, carbonic acid semi-morpholide, carbonic acid mono esters, benzoic acid and pyridine carboxylic acids which preferably are substituted or from saturated or unsaturated, in a given case, substituted by a morpholine group, low molecular weight aliphatic mono or dicarboxylic acids.

These compounds are stated to have an antiphlogistic and analgesic activity

Furthermore, there are known from Belgian Pat. No. 736,139 compounds of the following formula

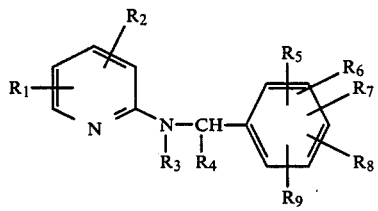

wherein $R_1$ is an amino group or an amino group substituted by low molecular weight alkyl groups having 1-6 carbon atoms or an amino group which is acylated by carbonic acid, by low molecular weight aliphatic carbonic acid monoester, by aromatic carbonic acid monoester, by saturated, straight or brach chain low molecular weight, aliphatic mono or dicarboxylic acids having 1-6 carbon atoms which in a given case is substituted or by the carbonic acid semi-morpholide or the carbonic acid semipiperidide, $R_2$ is a hydrogen atom or the same group as $R_1$, $R_3$ is a hydrogen atom or the lower molecular weight alkyl group having 1-6 carbon atoms or an acyl group as is given for the acylation of $R_1$, the groups $R_5$, $R_6$, $R_7$, $R_8$, and $R_9$ are the same or different and are hydrogen or halogen atoms, alkyl groups having 1-6 carbon atoms, trifluoromethyl groups, hydroxy groups, alkoxy groups having 1-6 carbon atoms, aliphatic acyl groups having 1-6 carbon atoms, carboxy groups or carboxyalkyl groups having 1-6 carbon atoms and $R_4$ is hydrogen or an alkyl group having 1-6 carbon atoms or the groups

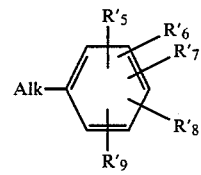

where Alk is a straight or branched alkylene group having 1-3 carbon atoms which in a given case, is substituted by a hydroxy group or alkyl group having 1-6 carbon atoms and the groups $R'_5$, $R'_6$, $R'_7$, $R'_8$, and $R'_9$ are the same or different and have the same meaning as the groups $R_5$-$R_9$, whereby at least one of the groups $R'_5$, $R'_6$, $R'_7$, $R'_8$, or $R'_9$ is not hydrogen if Alk is an unsubstituted alkylene group, and at least 3 of the groups $R_5$, $R_6$, $R_7$, $R_8$, or $R_9$ are not hydrogen, if $R_4$ is hydrogen or an alkyl group. These compounds also are stated to have an antiphlogistic and analgesic activity.

SUMMARY OF THE INVENTION

Compounds are prepared having the formula

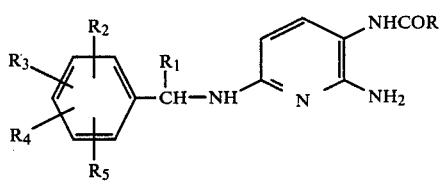

where R is a $C_1$-$C_4$ alkyl group, e.g. methyl, ethyl, propyl, isopropyl, butyl, sec.butyl or tert.butyl, a $C_1$-$C_4$ alkoxy group, e.g. methoxy, ethoxy, propoxy, isopropoxy, butoxy, or sec.butoxy group, a phenoxy group, a phenyl $C_1$-$C_2$-alkoxy group, $R_1$ is hydrogen or a $C_1$-$C_4$ alkyl group and R is hydrogen or a $C_1$-$C_4$ alkyl group and the groups $R_2$, $R_3$, and $R_4$ are the same or different and are hydrogen, trifluoromethyl, halogen atoms, e.g. chlorine, bromine, or fluorine $C_1$-$C_4$ alkyl groups, $C_1$-$C_4$ -alkylcarbonyl groups, the aminosulfonyl group ($NH_2$—$SO_2$—) or a $C_1$-$C_4$-alkylcarbonylamino group and their pharmaceutically acceptable acid addition salts. The compounds are useful to treat epilepsy.

In a preferred group of compounds for use in treating epilepsy $R_1$ is as defined above and $R_2$ is hydrogen, trifluoromethyl, halogen, a $C_1$-$C_4$ -alkylcarbonyl group, a $C_1$-$C_4$ -alkylcarbonylamino group or an aminosulfonyl group, the groups $R_3$ and $R_4$ are the same or different and are hydrogen, halogen atoms or $C_1$-$C_4$ alkyl groups and $R_5$ is hydrogen or a $C_1$-$C_4$ -alkyl group. In a still more preferred class of compounds R, $R_1$, and $R_2$ are as just defined and $R_3$, $R_4$, and $R_5$ are all hydrogen.

Another preferred group of compounds for treating epilepsy is that where R is a $C_1$-$C_4$ alkoxy group, $R_2$ is hydrogen, trifluoromethyl, halogen, a $C_1$-$C_4$ -alkylcarbonyl group, a $C_1$-$C_4$-alkylcarbonylamino group or an aminosulfonyl group and the groups $R_1$, $R_3$, $R_4$, and $R_5$ are hydrogen.

An additional preferred group of compound for treating epilepsy is that where R is a $C_1$-$C_4$ alkyl group, a phenoxy group or a phenyl-$C_1$-$C_2$ alkoxy group, $R_2$ is hydrogen, trifluoromethyl, halogen, a $C_1$-$C_4$-alkylcarbonyl group, a $C_1$-$C_4$-alkylcarbonylamino group or an aminosulfonyl group and the groups $R_1$, $R_3$, $R_4$, and $R_5$ are hydrogen.

Compounds of the formula

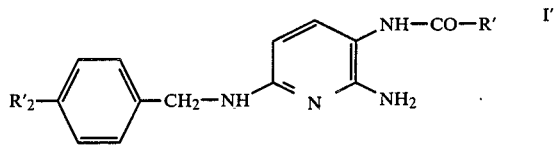

where $R'$ is a $C_1$-$C_4$-alkyl group, a $C_1$-$C_4$-alkoxy group, a phenoxy group or a phenyl-$C_1$-$C_2$-alkoxy group and $R'_2$ is a trifluoromethyl group, a $C_1$-$C_4$-alkylcarbonyl group, a $C_1$-$C_4$-alkylcarbonylamino group or an aminosulfonyl group ($NH_2SO_2$—) and $R'_2$ also is fluorine or hydrogen when $R'$ is a $C_1$-$C_4$ alkyl group, a phenoxy group or a phenyl-$C_1$-$C_2$-alkoxy group are new per se. Compounds within formula I' where $R'$ is as just defined and $R'_2$ is a trifluoromethyl group, an acetyl group, an acetylamino group or an aminosulfonyl group where $R'_2$ also can be fluorine or hydrogen in case $R'$ is a $C_1$-$C_4$-alkyl group, a phenoxy group or a phenyl-$C_1$-$C_2$-alkyl group is a preferred class. A still more preferred class within that just recited is where $R'$ is as defined and $R'_2$ is a trifluoromethyl group. A more limited preferred class is where $R'$ is a $C_1$-$C_4$-alkoxy group or a phenoxy group and $R'_2$ is a trifluoromethyl group. Another preferred class is where $R'$ is a $C_1$-$C_4$ alkyl group, a phenoxy group or a phenyl-$C_1$-$C_2$-alkoxy group and $R'_2$ is hydrogen or fluorine.

The compounds of formula I' can be produced by:

(a) reducing the nitro group to an amino group in a compound of the formula

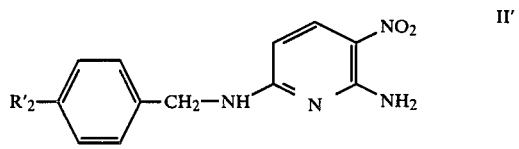

wherein $R'_2$ is as defined above and introducing the group R'CO by acylating the 3-position amino group, or (b) reacting a compound of the formula

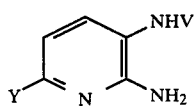

with a compound of the formula

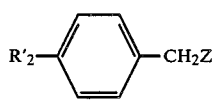

whereby V of formula III' is hydrogen or the group —COR' and Y is an amino group, in case Z is halogen V can be an amino group or the group —OW and where W is a hydrogen atom, a low molecular weight alkyl group, a phenyl, a phenyl group substituted by at least one halogen atom, nitro group or methyl group, or Z also can be an amino group if Y is halogen, a hydroxy group or the group OW, with or without a solvent, preferably in the presence of a condensation agent at elevated temperature or (c) simultaneously condensing and reducing a compound of formula III' where Y is the amino group and V is as defined, with a compound of the formula

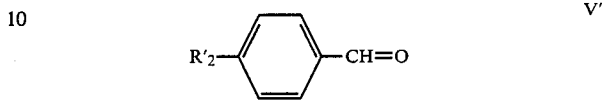

and in the compounds obtained according to processes (b) and (c) which have a free amino group in the 3-position of the pyridine ring, introducing the group R'CO— by acylation and in a given case, converting the compounds prepared into their acid addition salts.

The compounds of formula I have a marked antiepileptic action having longer life times in epileptic patients (for example 10 hours). This action is particularly surprising in view of the previously known state of the art mentioned at the beginning.

The groups $R_2$, $R_3$, $R_4$, and $R_5$ present in formula I in each case can be the same or different. In case the groups $R_2$, $R_3$, $R_4$, and $R_5$ are alkyl groups or alkylcarbonylamino groups, the alkyl group can be straight or branched. This is also true in regard to the groups R and $R_1$ in case these are alkyl or alkoxy groups. In case the groups $R_2$, $R_3$, and/or $R_4$ are halogen, it is a matter of preferably fluorine and chlorine. In case R is a phenyl-$C_1$-$C_2$-alkoxy, it is a matter of especially an ethoxy group which is substituted in the β-position (that is in the 2-position). The alkyl groups present as well as the alkoxy groups particularly consist of one or two C-atoms, that is it a matter with the groups R, as well as $R_1$ to $R_5$ in case the groups are alkyl groups, alkoxy groups or alkylcarbonyl-amino groups, they are preferably methyl, ethyl, methoxy, and ethoxy groups. In case the phenyl group (which contains the $R_2$ to $R_5$ groups) contains a substituent and this substituent is halogen, $CF_3$, $C_1$-$C_4$ alkylcarbonyl, $C_1$-$C_4$-alkylcarbonylamino or aminosulfonyl, this is preferably in 4 or 3-position of the phenyl ring; this is also true if this phenyl ring contains additional alkyl substituents. Alkyl substituents of the previously mentioned phenyl group preferably have them in the 2-positions and or the 4-positions of the phenyl ring.

Examples of the compounds of formula I with an antiepileptic action are:

2-amino-3-carbethoxyamino-6-benzylaminopyridine
2-amino-3-carbethoxyamino-6-(4-ethylbenzylamino)-pyridine
2-amino-3-carbethoxyamino-6-(3,5-dimethylbenzylamino)-pyridine
2-amino-3-carbethoxyamino-6-(4-acetylbenzylamino)-pyridine
2-amino-3-carbethoxyamino-6-(α-methyl-4-fluoro-benzylamino)-pyridine
2-amino-3-carbethoxyamino-6-(4-fluorobenzylamino)-pyridine
2-amino-3-carbethoxyamino-6-(3-fluorobenzylamino)-pyridine
2-amino-3-carbethoxyamino-6-(4-chlorobenzylamino)-pyridine 2-amino-3-carbethoxyamino-6-(4-aminosulfonyl-benzylamino)-pyridine
2-amino-3-carbethoxyamino-6-(4-trifluoromethyl-benzylamino)-pyridine
2-amino-3-carbethoxyamino-6-(4-methylcarbonylamino-benzylamino)-pyridine
2-amino-3-carbethoxyamino-6-(2,4,6-trimethyl-benzylamino)-pyridine
2-amino-3-carbethoxyamino-6-(3,4,6-trimethyl-benzylamino)-pyridine
2-amino-3-carbethoxyamino-6-(2,3,4-trimethyl-benzylamino)-pyridine
2-amino-3-carbethoxyamino-6-(2,4,6-triethyl-benzylamino)-pyridine
2-amino-3-carbethoxyamino-6-(2,6-dimethyl-4-ethyl-benzlamino)-pyridine
2-amino-3-carbethoxyamino-6-(2-fluoro-4-methyl-benzylamino)-pyridine
2-amino-3-carbethoxyamino-6-(2,4-dimethyl-chloro-benzylamino)-pyridine
2-amino-3-carbethoxyamino-6-(2,4,6-dimethyl-5-fluoro-benzylamino)-pyridine
2-amino-3-carbethoxyamino-6-(2,4,6-trimethyl-3-fluoro-benzylamino)-pyridine
2-amino-3-acetylamino-6-(4-fluoro-benzylamino)-pyridine
2-amino-3-phenoxycarbonylamino-6-benzylamino-pyridine
2-amino-3-phenoxycarbonylamino-6-(4-fluorobenzylamino)-pyridine
2-amino-3-phenethoxycarbonylamino-6-benzylamino-pyridine
2-amino-3-phenethoxycarbonylajino-6-(3-trifluoromethyl-benzylamino)-pyridine.

The antiepileptic activity of the compounds of formula I is measurable in animal experiments as an anticonvulsive action. The compounds of formula I therefore show at the maximum electroshock on the mouse a good anticonvulsive action.

For example in the above-mentioned experimental methods at a dosage of 40 mg/kg of body weight of the mouse there occurs the anticonvulsive action. This anticonvulsive action is comparable with the action of the known drug "Valproate" (valproic acid salt). The lowest effective dosage in the above-mentioned animals experiments is for example:

0.2 mg/kg orally
0.05 mg/kg intravenously

As a general dosage range for the anticonvulsive effect in the mouse there can be used for example:

0.2–2000 mg/kg orally, especially 40 mg/kg,
0.05–500 mg/kg intravenously, especially 10 mg/kg.

The compounds of the invention are indicated for the treatment of epilepsy.

Individually the results of the anticonvulsive action of the compounds of formula I for example are seen from the following table:

TABLE 1

Anticonvulsive Action of Compounds of Formula I
With the Mouse Expressed as ED 50 in mg/kg
With Intraperitoneal Application

| Compound Cipher-Number | TD 50 | Maximum Electro-Shock (MES) ED 50 | Metrazole-Test (MET) ED 50 |
| --- | --- | --- | --- |
| D 7175 | 45.6 | 19.7/2.3 | 9.46/4.8 |
| D 10 328 | 1.09 | 1.97/0.55 | 1.01/1.08 |
| D 10 981 | 32.7 | 17.2/1.90 | 9.07/3.61 |
| D 11 208 | 76.3 | 27.9/2.73 | 11.2/6.81 |

TABLE 1-continued

Anticonvulsive Action of Compounds of Formula I
With the Mouse Expressed as ED 50 in mg/kg
With Intraperitoneal Application

| Compound Cipher-Number | TD 50 | Maximum Electro-Shock (MES) ED 50 | Metrazole-Test (MET) ED 50 |
| --- | --- | --- | --- |
| D 9663 | 142.3 | 123.8/1.15 | 57.2/2.49 |
| D 9389 | 23.9 | 14.6/1.64 | 10.0/2.39 |
| D 9998 | 37.7 | 22.5/1.67 | 20.3/1.86 |
| D 13 223 | 201.0 | 84.3/2.38 | 93.8/2.14 |
| D 10 558 | 73.9 | 53.8/1.37 | 18.4/4.0 |
| D 9805 | 529.6 | 107.7/4.9 | 549.8/0.96 |

TD 50: is the ED 50 for the behavior of the mouse on the experimental model of the rotating rod in mg/kg with intraperitoneal application. The TD 50 is a measure for the undesired neurotoxic side effect.

The numbers below the slanting line in columns 3 and 4 in each case means the quotient TD 50/ED 50. Thus they give the therapeutic breadth in reference to the undesired neurotoxic side action (measured on the model of the rotating rod).

Compounds according to code number:

D 7175: 2-amino-3-carbethoxyamino-6-benzylamino-pyridine-hydrochloride

D 10 328: 2-amino-3-carbethoxyamino-6-(2,4,6-trimethyl-benzylamino)pyridine-hydrochloride D 10 981: 2-amino-3-carbethoxyamino-6-(3-fluorobenzylamino)-pyridine-hydrochloride D 11 208: 2-amino-3-carbethoxyamino-6-(4-trifluoromethyl-benzylamino)-pyridine-hydrochloride D 9663: 2-amino-3-carbethoxyamino-6-(4-methylcarbonylamino-benzylamino)-pyridine-hydrochloride D 9389: 2-amino-3-carbethoxyamino-6-(4-chlorobenzylamino)-pyridine-hydrochloride D 9998: 2-amino-3-carbethoxyamino-6-(4-fluorobenzylamino)-pyridine-hydrochloride D 13 223: 2-amino-3-acetamino-6-(4-fluoro-benzylamino)-pyridine-hydrochloride D 10 558: 2-amino-3-carbethoxyamino-6-(4-methylcarbonyl-benzylamino)-pyridine D 9805: 2-amino-3-carbethoxyamino-6-(4-aminosulfonyl-benzylamino)-pyridine.

DESCRIPTION OF THE EXPERIMENTAL METHODS FOR TESTING THE ANTICONVULSIVE ACTION

All experiments were carried out with male Carworth Farms Mice.

The materials were tested in three dosages (30, 100, 300 mg/kg) (600 mg/kg was co-tested if a sufficient amount of the material was present). The materials in each case were dissolved in 30% aqueous polyethylene glycol solution.

1. MES—Maximum Electroshock Attack Test

A maximum electroshock attack was obtained through alternating current (60 Hz, 50 m A intensity) with which the mouse was irritated for 0.2 seconds via corneal electrodes. A 5–7 times weaker intensity of irritation was sufficient to produce a minimum electroshock-attack. One drop of 0.9% aqueous NaCl solution was given before applying the electrodes into the eyes in order to guard against killing the animals. The test substances were dispersed intraperitoneally before the irritation. Raising the tonic stretching components of the attack (rear extremities) was regarded as protective action. The results were represented as follows:

number of animals having protective action/total number of test animals

2. s.c. Met—Subcutaneous Pentetrazole—Results—Swelling Test 85 mg/kg of pentetrazole (produced attack in more than 95% of the mice results) were applied subcutanuously as a 0.5% solution (below the skin of the neck). The animal was observed for 30 minutes. The absence of a clearly noticeable attack, (single occurrence of a chronic spasm lasting 5 seconds) based on the previous intraperitoneal application of the test substances evaluated as protective action (the test substances were applied intraperitoneally before the application of pentetrazole). The results were represented as follows: number of animals having protective action/total number of test animals

3. TD 50—Neurotoxicity Activity

The test on the rotating rod was referred to for the evaluation of the neurotoxicity. The animals were placed on a rotating (6 rotations per minute) plastic rod having a diameter of 2.54 cm. Normal untreated mice could remain unlimitedly on the rod rotating at this speed. An animal was characterized as neurologically toxic if it fell from the rotating rod within one minute.

number of animals which fell/total number of test animals

Examples for the toxicity on the mouse per se (expressed as LD 50 in mg/kg are as follows:

| Code Number | LD 50/ Mouse Per os |
| --- | --- |
| D 7175 | 402 |
| D 10 328 | 127 |
| D 10 981 | 2061 |
| D 9389 | 1250–1500 |
| D 9998 | 617 |

The determination of the oral toxicity on the white mouse was carried out in the international procedure according to Miller & Tainter (Proc. Soc., Exper. Biol. a Med. Vol. 57, page 261 et. seq. (1944)) with an observation time of 24 hours. The toxicity was stated as LD 50 in mg/kg. The LD 50 is that dosage at which 50% of the animals employed are killed.

The pharmaceutical preparations generally can contain between 0.2 to 2000, preferably 40 to 300 mg of the active component (or components) of the invention.

The dispensation can be carried out for example in the form of tablets, capsules, pills, dragees, plugs, salves, jellies, creams, powders, dusts, aerosols, or in liquid form. As liquid forms of the use there can be employed for example oily or alcoholic or aqueous solutions as well as suspensions and emulsions. Preferred forms of use are tablets which contain between 0.2 and 2000 mg or solution which contains 0.5 to 30% of active material.

The individual doses of the active components of the invention for example can be:

(a) with oral forms of medicine between 0.2 to 2000 mg, preferably 10 to 300 mg, especially 40 to 200 mg;

(b) with parenteral forms of medicine (for example intravenously, intramuscularly) between 0.05 to 500 mg, preferably 10 mg;

(c) with forms of medicine of reactal or vaginal application between 0.5 to 5000, preferably 50 mg.

In each case the doses are based on the free base.

For example there can be recommended 3 times daily 1 to 4 tablets having a content of 0.2 to 2000 mg of active material or for example by intravenous injection 1 to 4 times daily one amploule having 1 to 5 ml content with 5 to 1500 mg of substance. By oral dispensation the minimum daily dosage is for example 10 mg; the maximum daily dosage by oral dispensation should not exceed 4000 mg.

For example there can be recommended dosages according to Table 2:

TABLE 2

| Compound | Individual Dosage In mg, For Example Can Be Dispensed 1–3 Times Daily | Maximum Daily Dosage In mg |
| --- | --- | --- |
| D 9998 | 100–300 | 800 |
| D 7175 | 100–300 | 800 |
| D 10 328 | 10–50 | 150 |
| D 10 981 | 100–300 | 2000 |
| D 11 208 | 100–300 | 800 |
| D 9663 | 300–500 | 1000 |
| D 9389 | 80–200 | 1500 |
| D 13 223 | 200–600 | 3000 |
| D 10 558 | 100–300 | 800 |
| D 9805 | 200–400 | 3000 |

The accute toxicity of the compounds of the invention on the mouse (expressed by the LD 50 mg/kg; method according to Miller & Tainter, Proc. Soc. Exper. Biol. a Med. Vol. 57 (1944), pages 261 et. seq.) is for example with oral application between 10 and 10,000 mg/kg (or above 10000 mg/kg).

The compounds of formula I are suitable for the production of pharmaceutical compositions and preparations for the treatment of epilepsy in mammals, e.g. humans. The pharmaceutical compositions or medicaments contain, as active principle, one or more of the compounds of Formula I, optionally in admixture with other pharmacologically or pharmaceutically active substances. The medicaments may be prepared in known manner with the known and usual pharmaceutical assistants, as well as other customary carriers and diluents.

As carriers and assistants, for example, are those recommended or given in the following literature as adjuvants for pharmacy, cosmetic, and related fields such as in Ullmann's Encyklopadie der technischen Chemie, Vol. 4 (1953), pages 1–39; Journal of Pharmaceutical Sciences 52 (1963), pages 918 et seq.; H. v. Czetsch-Lindenwald, Hilfsstoffe fur Pharmazie und angrenzende Gebiete; Phar. Ind. 2 (1961), pages 72 et seq.; Dr. H. P. Fiedler, Lexicon angrenzende Gebiete, Cantor Kg. Aulendorf in Wurttemberg (1971).

Examples of such materials include gelatin, natural sugars such as sucrose or lactose, lecithin, pectin, starch (for example cornstarch), alginic acid, tylose, talc, lycopodium, silica (for example collodial silica), glucose, cellulose, cellulose derivatives for example, cellulose ethers in which the cellulose hydroxyl group are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions, there can be used water of physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g. glyceryl oelate glyceryl stearate, glyceryl palmitate, and glyceryl acetate, partial esters of glycerine, e.g., glyceryl monostearate, glyceryl distearate, glyceryl monopalmitate, paraffins, and the like In the production of the preparation, there can be used known and customary solution aids or emulsifiers. As solution aids and emulsifiers, there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyoleotriglycerides, linolized oleotriglycerides, polyethylene oxide-condensation products of fatty alcohols, alkylphenols or fatty acids or also 1-methyl-3-(2-hydroxyethyl)-imidazolidone-2. As used herein, polyoxyethylated means that the materials in question contain polyoxyethylene chains whose degree of polymerization generally is between 2 and 40, particularly between 10 and 20.

Such polyoxyethylated materials, for example can be obtained by reaction of hydroxyl group containing compounds (for example, monodiglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives stabilizers, buffers, for example, calcium hydrogen phosphate, collodial aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

The pharmacological and galenical treatment of the compounds of the invention takes place according to the usual standard methods For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides reference is made to the following standard work: Sucker, Fuchs, Speiser, Pharmazeutische Technologie, Thieme-Verlag Stuttgart, 1978.

The application of active material or drug can take place on the skin of mucous membrane or internally, for example, orally, parenterally, pulmonarily, rectally, nasally, vaginally, perlingually, intravenously, intraarterially, intracardially, intramuscularly, intraperitoneally, intrascutaneously, or subcutaneously.

The addition of other medicines is also possible or favorable.

The production of compounds of formula I can be carried out according to Belgium Pat. Nos. 698,384, 764,362, and 736,139 respectively in a manner analogous to the stated process given in the three Belgian patents. In the examples, there is described the production of several compounds. Naturally, the production can be carried out using the novel process of the invention set forth supra.

Depending on the process conditions and starting materials, there are obtained compounds according to the invention (or used in the invention) of formula I in free form or in the form of their salts. The salts of course should be pharmaceutically acceptable salts. These salts can be converted in known manner into the free base, for example, using an alkali, e.g. sodium hydroxide or potassium hydroxide, or using an ion-exchange resin, e.g. containing quaternary ammonium groups. The salts can be obtained again from the free base by reaction with organic or inorganic acids. As such acids, there can be mentioned for example, hydrohalic acids, e.g. hydrochloric acid, hydrobromic acid and hydriodic acid, sulfuric acid, acids of phosphorus, e.g. phosphoric acid and phosphorous acid, nitric acid, perchloric acid, organo mono, di, or tricarboxylic acids of the aliphatic, alicyclic aromatic or heterocyclic series as well as sulfonic acids. Examples of these are alkanoic acids such as formic acid acetic acid, propionic acid, valeric acid, alkanedioc acids, e.g. succinic acid, malonic acid, oxalic acid, and adipic acid, hydrocarboxylic acid, e.g. glycolic acid, lactic acid, malic acid, tartaric acid, citric acid, and ascorbic acid, maleic acid, fumaric acid, hydroxymaleic acid, pyruvic acid, phenylacetic acid, benzoic acid, p-aminobenzoic acid, anthranilic acid, p-hydroxybenzoic acid, salicylic acid or p-aminosalicylic acid, embonic acid, alkanesulfonic acid, e.g. methanesulfonic acid, ethanesulfonic acid and butanesulfonic acid, hydroxyalkanesulfonic acids, e.g. hydroxyethanesulfonic acid, ethylenesulfonic acid, halobenzenesulfonic acids, e.g. o-chlorobenzenesulfonic acid, p-chlorobenzenesulfonic acid, m-chlorobenzenesulfonic acid, o-bromobenzenesulfonic acid, p-bromobenzenesulfonic acid, toluenesulfonic acid, e.g. p-toluenesulfonic acid, o-toluenesulfonic acid or m-toluenesulfonic acid, benzenesulfonic acid, naphthalenesulfonic acid, e.g. alpha naphthalenesulfonic acid or beta naphthalenesulfonic acid, or sulfanilic acid.

The conversion of a salt of a compound of the formula I into another salt is described for example, in Example 10.

The compounds obtained which contain optically active carbon atoms and as a rule are obtained as the racemate can be resolved into the optically active isomers in manner known of itself, for example, by means of an optically active acid.

However, it is also possible initially to employ optically active or also diastereomeric starting materials in which case as end product there is then obtained a corresponding pure optically active form or diastereomeric configuration.

As previously indicated the invention also includes a new group of compounds of formula I'. These compounds of formula I' represent a smaller group of compounds within the group of compounds of formula I, of which as indicated a large number are already known compounds. The compounds of formula I' likewise possess the marked antiepileptic activity with longer half life times in epileptic patients (for example, 10 hours). This action, especially in view of the known state of the art mentioned above is surprising.

In the event that the group $R'_2$ of formula I' is an alkylcarbonyl group or an alkylcarbonylamino group, the alkyl group can be straight chain or branched. The same is true in regard to the group R' of formula I, in case there is an alkyl or alkoxy group. In case R' is a phenyl-$C_1$-$C_2$-alkoxy group, it is especially a mater of an ethoxy group is substituted in the β-position (that is in the 2-position) by the phenyl group (2-phenylethyl(1)-oxy group). The alkyl groups as well as the alkoxy groups present especially consist of one or two C-atoms, that is it is a matter of the groups R', as well as $R'_2$ in case these represent alkyl groups, alkoxy groups, alkylcarbonyl groups, or alkylcarbonylamino groups, preferably they are methyl, ethyl, methoxy, and ethoxy groups.

Examples of new compounds of formula I' with antiepileptic activity are:
2-amino-3-carbethoxyamino-6-(4-acetylbenzylamino)-pyridine
2-amino-3-carbethoxyamino-6-(4-aminosulfonyl-benzylamino)-pyridine
2-amino-3-carbethoxyamino-6-(4-trifluoromethyl-benzylamino)-pyridine
2-amino-3-carbethoxyamino-6-(4-methylcarbonylamino-benzylamino)-pyridine
2-amino-3-acetylamino-6-(4-fluorobenzylamino)-pyridine
2-amino-3-phenoxycarbonylamino-6-benzylamino-pyridine
2-amino-3-phenoxycarbonylamino-6-(4-fluoro-benzylamino)-pyridine
2-amino-3-phenethoxycarbonylamino-6-benzylamino-pyridine
2-amino-3-phenethoxycarbonylamino-6-(3-trifluoromethyl-benzylamino)-pyridine.

The toxicity of the compounds of formula I' on the mouse per os (expressed as LD 50 in mg/kg) is for example between 100–2000.

Process (a)

For the reduction according to process (a) mentioned above there has proven especially suited catalytic hydrogenation. As catalysts for example there can be employed Raney-nickel, noble metals such as palladium and platinum as well as their compounds, with or without carrier, as for example, barium sulfate, calcium sulfate, etc. It is recommended to carry out the hydrogenation of the nitro group at temperatures between 20° and 100° C. and a pressure of approximately 1 to 70 bar in a solvent. As solvents there are suited for example $C_1$-$C_4$-alkanols, e.g. methanol, ethanol, propanol, isopropanol, butanol, cyclic ethers such as dioxane and tetrahydrofurane, methoxyethanol, water, aromatic hydrocarbons (e.g. benzene, toluene, xylene) as well as mixtures of these agents. For the subsequent isolation of the reduced compounds in many cases it can be advantageous if there is added to the hydrogenating mixture at the beginning a drying agent such as anhydrous sodium or magnesium sulfate.

However, the reduction can also be carried out with nascent hydrogen, for example zinc/hydrochloric acid, tin/hydrochloric acid, iron/hydrochloric acid, or with salts of hydrogen sulfide in alcohol/water at about 70° to about 120° C. or with activated aluminum in water containing ether at 20° to 40° C. or with tin (II) chloride/hydrochloric acid.

In case there is employed a starting material which contains an oxo group (for example alkylcarbonyl), it can be suitable to protect this oxo group through customary acetal formation (for example in the form of the ethylene acetal). This is particularly true for the catalytic hydrogenation.

The thus obtained reaction product is suitably immediately reacted in the resultant reaction mixture with a compound which is suited to replace a hydrogen atom of the amino group in the 3-position obtained in the reduction by the group —COR', without it being necessary to isolate the 2,3-diamino-6-benzylamino-pyridine derivative. This is especially true for the case of the catalytic hydrogenation. It is of course understood that this last mentioned compound can also be isolated and the R'CO group introduced. The introduction of the R'CO group can be carried out in the customary method for this with the customary reagents. For example, there are for such reagents: haloformic acid ethyl esters such as ethyl chloroformate, bromoformate or iodoformate, phenyl chloroformate, bromoformate, or iodoformate or phenyl $C_1$-$C_2$-alkyl esters of chloroformic, bromoformic, or iodoformic acid. In case R' is a $C_1$-$C_4$-alkyl group there come into question as acylating agent for example the halides (chloride, bromide, iodide) or anhydrides of the $C_1$-$C_4$-alkanecarboxylic acids, e.g. formic acid, acetic acid, propiomic acid or butyric acid. Since the free amine of formula I' wherein the group —COR' is hydrogen are acid sensitive, it is suitable to work under a nitrogen atmosphere.

The introduction of the R'CO group is generally carried out in an inert solvent or suspension agent at temperatures between 0° to 60° C., especially 5° to 40° C., preferably 20° to 25° C. As solvents there can be employed for example: saturated alicylic and cyclic ethers (dioxanes, tetrahydrofurane, lower dialkyl ethers such as diethyl ether, diisopropyl ether), lower alkanols such as ethanols, isopropanol, butanol, lower aliphatic ketones (e.g. acetone, methyl ethyl ketone), lower aliphatic hydrocarbons (e.g. hexane, octane) or halohydrocarbons (e.g. methylene chloride, chloroform, 1,2-dichloroethane), aromatic hydrocarbons (e.g. benzene, toluene, xylene), lower dialkylamides of lower saturated aliphatic carboxylic acids (e.g. dimethyl formamide, dimethyl acetamide), tetramethyl urea, N-methyl pyrrolidone, dimethyl sulfoxide or mixtures of these agents.

Generally the reactants are reacted in equimolar amounts. In a given case, however, it can be suitable to add one reactant in a slight excess. Also in a given case the reaction can be carried out in the presence of basic or acid binding agents, such as alkali carbonates (e.g. potassium carbonate, sodium carbonate), alkali hydrogen carbonates (e.g. sodium bicarbonate or potassium bicarbonate), alkali acetates (e.g., sodium acetate or potassium acetate), alkali hydroxides (e.g. sodium hydroxide or potassium hydroxide) or tertiary amines (for example triethylamine). The latter is especially true if haloformic acid esters are employed.

The starting materials of formula II' are known or can be obtained through reaction of 2-amino-3-nitro-6-chloropyridine with amines of the formula:

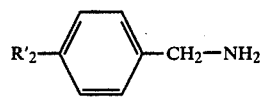

with or without solvent at temperatures between 0° to 200° C., in a given case, in the presence of an additional acid acceptor analogous to the method described in Belgian patents Nos.698,384, 764,362, or 736,139 or according to German patent No. 1,795,797, the entire disclosures of these four patents are hereby incorporated by reference and relied upon.

Processes (b) and (c)

Process (b) mentioned above is suitably carried out at temperatures between 80° to 250° C., whereby if Z is a hydroxy group, in a given case, even higher temperatures up to 400° C. are necessary. Procedure (c) mentioned above is suitably carried out at temperatures between 20° to 150° C.

As solvents for processes (b) and (c) for example, there can be used water, alcohols, e.g. any of those mentioned above, benzene, toluene, dioxane, dimethyl formamide, N-methyl pyrrolidone, dimethyl sulfoxide, sulfolane, tetramethyl urea, etc.

As condensation agents which can be employed for process (b) if Z or Y is a halogen atom, the most important for example, are sodium acetate, sodamide, alkali carbonates, e.g. sodium carbonate and potassium carbonate and tertiary amines, e.g. triethylamine. Zinc chloride, phosphorus oxychloride, p-toluenesulfonic acid, iodine and the like for example, can serve as condensation agents if Z is an amino group. Zinc chloride, calcium chloride and triethyl phosphate for example, can be used if Z or Y is a hydroxyl group or the group —OW. In a given case, the subsequent acylation of the amino group in the 3-position (introduction of R'CO—) can be carried out according to the known methods with the corresponding esters (see for example the recitation in connection with process (a)).

Starting materials of formula III' wherein V is the group R'CO—and Y is the amino group can be obtained from 2,3,6-triaminopyridine by introduction of the R'CO— group (in this connection, see process (a) above 1). Starting materials of formula III' wherein Y is halogen can be obtained by reaction of 2-amino-3-nitro-6-chloro-pyridine and subsequent introduction of the group R'CO. For production of the corresponding starting compound which have a bromine atom in the 6-position, for example the 2-amino-3-nitro-6-chloropyridine is heated with a saturated, aqueous-alcoholic ammonia solution in an autoclave at 100° to 120° C. for several hours (2 to 4) and the 6-aminopyridine derivative formed thereby then diazotized in known manner and reacted according to the conditions of the Sandmeyer reaction or modified Sandmeyer reaction in the presence of bromide ions and/or corresponding copper (I) salts (CuBr, CuCl) with heating. As solvents for this purpose there are suited water-alcohol mixtures or mixtures of water, dimethyl formamide and dimethyl sulfoxide.

Starting materials of formula III wherein Y is a hydroxy group, a lower alkoxy group or a phenoxy group can be obtained for example as follows: 2,6-dichloro-3-nitro-pyridine is reacted with one equivalent of a lower alcoholate, e.g. sodium ethylate or alkali phenolate, e.g. sodium phenolate, or one equivalent of alkali, e.g. sodium hydroxide, in a given case in the presence of a tertiary amine, e.g. triethylamine, in a polar solvent (lower alcohols, e.g. those mentioned above, tetrahydrofuran) at temperatures between −50° to +100° C., preferably between −50° and +10° C. and the nitro group in the compound obtained reduced to the amino group by hydrogenation in the presence of Raney-nickel or other noble metal catalysts such as palladium or platinum, for example at temperatures between 20° and 150° C. in a solvent such as alcohols, e.g. any of those mentioned above, dioxane, tetrahydrofuran. In the thus obtained compounds in a given case, the group R'CO— then can be introduced by reaction with the corresponding acid halide (in this connection see process (a) above).

Unless otherwise indicated all parts and percentages are by weight.

The composition can comprise, consist essentially of, or consist of the stated materials, and the can comprise, consist essentially of, or consist of the recited steps with the stated materials.

EXAMPLE 1

2-amino-3-carbethoxyamino-6-(α-methyl-4-fluorobenylamino)-pyridine

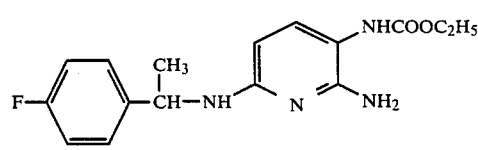

35 grams of 2-amino-3-nitro-6-(α-methyl-4-fluorobenzylamino)-pyridine were hydrogenated with 10 grams of Raney-nickel and 30 grams of magnesium sulfate in 500 ml of dioxane in an autoclave at 55° C. The catalyst then was filtered off with suction under nitrogen, washed with a little dioxane and the filtrate treated with 13.8 ml of ethyl chloroformate. The reaction product was precipitated from the solution, with ether and gasoline as an oil. The oily compound was taken up in water, made alkaline with 2N aqueous sodium hydroxide and the base extracted with ether. The ethereal phase was treated with isopropanolic hydrochloric acid whereby a syrup-like precipitate came out which crystallized out after 2 hours. The cystals of the hydrochloride were filtered off with suction, washed well with anacetone/ether mixture and subsequently dried.

Yield: 35 grams

Melting Point of the hydrochloride 160° C.

Analogous to Example 1 the nitro compounds of the formula

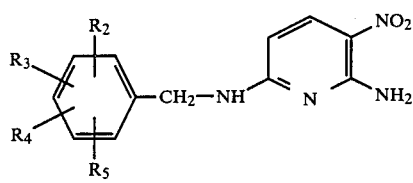

set forth in Table 3 were hydrogenated in the presence of Raney-nickel and magnesium sulfate under a hydrogen pressure of 40 bar (unless another pressure is given) and subsequently reacted with ethyl chloroformate to the final compounds

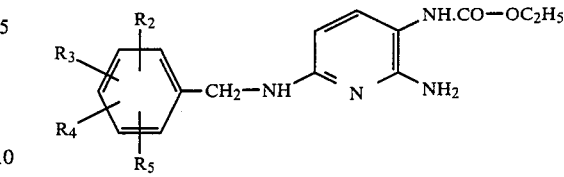

(Examples 2-7). In Example 8 in place of ethyl chloroformate acylation was with acetyl chloride; therefore there was obtained as the final product the 2-amino-3-acetamino-6-(4-fluoro-benzylamino)pyridine. In Example 9 after the hydrogenation acylation was with phenylethyl chloroformate, there was obtained here 2-amino-3-phenylethoxy-carbonylamino-6-benzylamino-pyridine.

In column 8 of Table 3 there is given the working up after the addition of the acylating agent. In case this is not given in column 7 this means that the final product after addition of the ethyl chloroformate or the phenylethyl chloroformate or the acetyl chloride crystallized out of the reaction mixture in the form of the hydrochloride (immediately or in the course of 1-12 hours). In those cases the final product was filtered off with suction, washed, dried in a vacuum and in a given case, recrystallized. In case the final product was recrystallized the solvent used is stated in column 7 of Table 3.

TABLE 3

| Example No. | $R_2$, $R_3$, $R_4$, $R_5$ | Nitro-Compound II g | Ra—Nickel/ MgSO$_4$ in g | Temperature of the hydrogenation | Ethyl Chloroformate ester ml | Melting point of the final product °C. as hydrochloride | Yield g | Working up |
|---|---|---|---|---|---|---|---|---|
| 2 | CF$_3$—⟨phenyl⟩— | 8,5 | 6/20 | 40° C. | 3 | 200 | 9 | |
| 3 | F (on phenyl) | 25 | 5/20 | 50° C. | 9,3 | 205 | 26 | |
| 4 | CH$_3$CO—NH—⟨phenyl⟩— | 12 | 9/30 | 90° C. | 4,5 | 211-212 | 8 | The reaction product came out oily and crystallized after standing for a short time, recrystallization first from water then from isopropanol |
| 5 | NH$_2$SO$_2$—⟨phenyl⟩— | 65 | 30/60 | 80° C. | 22,2 | 168-171 | 45 | As in Example 4, additional addition of ether recrystallized from methanol |
| 6 | CH$_3$—⟨phenyl with F⟩— | 42,5 | 15/30 | 40° C. | 16,8 | 212-213; Methanol | 26 | Filtered with suction after 12 hours |

TABLE 3-continued

| Example No. | Nitro-Compound II g | Ra—Nickel/MgSO4 in g | Temperature of the hydrogenation | Ethyl Chloroformate ester ml | Melting point of the final product °C. as hydrochloride | Yield g | Working up |
|---|---|---|---|---|---|---|---|
| 7 CH3CO—⌬— (1) | 44,5 | 30/60 | 60° C. | 16,5 | 203–206 | 10 | Inoculation and filtering with suction after standing overnight |
| 8 F—⌬— | 46 | 35/35 | 65° C.; 64 bar | 15,7 Acetylchloride | 247–249; Methanol | 6 | |
| 9 ⌬— | 99 | 30/40 | 50° C.; 20 bar | 80 phenylethyl chloroformate | 199; Methanol | | |

(1)As starting compound II there was employed the protected keto compound (in form of the ethylene acetate)

EXAMPLE 10

2-amino-3-carbethoxyamino-6-(2,4,6-trimethylbenzylamino)-pyridine-(1/3 citrate)

40 grams of 2-amino-3-carbethoxyamino-6-(2,4,6-trimethylbenzylamino)-pyridine hydrochloride were dissolved in 200 ml of methanol and treated with 25% aqueous ammonia, whereupon the base crystallized out. The base was filtered off with suction and dissolved in dioxane/methanol (2:1 by volume) in the hot. The warm solution was acidified with a solution of citric acid in methanol to pH 3, whereupon the "citrate" precipitated in cooling with stirring. The compound crystallized with 0.33 mole of citric acid and was recrystallized from a little isopropanol.

Yield: 33 grams
Melting Point: 131°–137° C.

EXAMPLE 11

2-amino-3-phenoxycarbonylamino-6-(4-fluorobenzylamino)-pyridine 24.3 grams of 2-amino-3-nitro-6-(4-fluorobenzylamino)-pyridine were hydrogenated with 18 grams of Raney-nickel and 18 grams of magnesium sulfate in 250 ml of dioxane at 65° C. under a pressure of 7.5 bar. Subsequently the product was filtered with suction from the catalyst under nitrogen, washed with a little dioxane and the filtrate treated under nitrogen with 17.1 grams of phenyl chloroformate. The reaction product crystallized out after a short time and was filtered off with suction. The compound was recrystallized from methanol under addition of carbon and dried in a vacuum.

Yield: 25 grams
Melting Point of the Hydrochloride: 210°–211° C.

EXAMPLE OF PHARMACEUTICAL PREPARATIONS

Tablets 10 kg of 2-amino-3-carbethoxyamino-6-(4-fluoro-benzylamino)-pyridine maleate were mixed with 2.5 kg of calcium hydrogen phosphate and 2.5 kg of cornstarch and the mixture granulated with a solution of 1 kg of polyvinyl pyrrolidone in 4 kg of demineralized water in known manner. After the mixing in of 1.3 kg of cornstarch, 2 kg of microcrystalline cellulose, 0.6 kg of magnesium stearate and 0.1 kg of highly dispersed silica there were molded tablets with a weight of 200 mg, a diameter of 9 mm and a radius of curvature of 10 mm and having a breaking notch. The resistance to rupture of the tablets was 80–100 Newton (Schleuniger resistance to rupture tester). The decomposition time according to DAB 8 was 5 minutes. Each tablet contained 100 mg of active material.

Capsules

Analogous to the above-described method of production for tablets there was produced a capsule filling which were filled into hard gelatin capsules of suitable size. Filling amount per capsule: 200 mg. One capsule contains 100 mg of active material.

What is claimed is:

1. A method of combatting epilepsy comprising administering to a mammal in need thereof an effective amount for the treatment of epilepsy of a compound of the formula

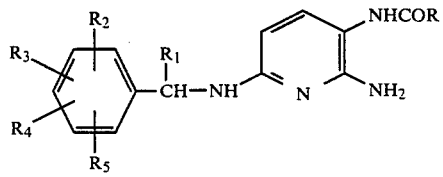

where R is a $C_1$–$C_4$ alkyl group, a $C_1$–$C_4$ alkoxy group, a phenoxy group, or a phenyl $C_1$–$C_2$-alkoxy group, $R_1$ is hydrogen or a $C_1$–$C_4$ alkyl group and $R_5$ is hydrogen or a $C_1$–$C_4$ alkyl group and the groups $R_2$, $R_3$ and $R_4$ each is hydrogen trifluoromethyl, halogen, a $C_1$–$C_4$ alkyl group, a $C_1$–$C_4$-alkylcarbonylamino group, an aminosulfonyl group, a $C_1$–$C_4$-alkylcarbonyl group, or its pharmaceutically acceptable acid addition.

2. A method according to claim 1 wherein $R_2$ is hydrogen, trifluoromethyl, halogen, a $C_1$–$C_4$-alkylcarbonyl group, a $C_1$–$C_4$-alkylcarbonylamino group or an aminosulfonyl group, the groups $R_3$ and $R_4$ each is hydrogen, halogen or a $C_1$–$C_4$ alkyl group and $R_5$ is hydrogen or a $C_1$–$C_4$-alkyl group.

3. A method according to claim 2 wherein $R_3$, $R_4$, and $R_5$ are all hydrogen.

4. A method according to claim 1 wherein R is a $C_1$–$C_4$ alkoxy group, $R_2$ is hydrogen, trifluoromethyl, halogen, a $C_1$–$C_4$ alkylcarbonyl group, a $C_1$–$C_4$-alkylcarbonylamino group or an aminosulfonyl group and each of $R_1$, $R_3$, $R_4$, and $R_5$ is hydrogen.

5. A method according to claim 1 wherein R is a $C_1$–$C_4$ alkyl group, a phenoxy group or a phenyl-$C_1$–$C_2$ alkoxy group, $R_2$ is hydrogen, trifluoromethyl, halogen, a $C_1$–$C_4$-alkylcarbonyl group, a $C_1$–$C_4$-alkyl-carbonylamino group or an aminosulfonyl group and each of $R_1$, $R_3$, $R_4$, and $R_5$ is hydrogen.

6. A method of combatting epilepsy comprising administering to a mammal in need thereof an effective amount for the treatment of epilepsy of a compound having antiepileptic action and having the formula

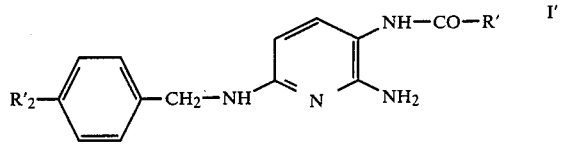

where R′ is a $C_1$–$C_4$-alkyl group, a $C_1$–$C_4$-alkoxy group, a phenoxy group or a phenyl-$C_1$–$C_2$-alkoxy group and $R'_2$ is a trifluoromethyl group, a $C_1$–$C_4$-alkylcarbonyl group, a $C_1$–$C_4$-alkylcarbonylamino group or an aminosulfonyl group with the proviso that $R'_2$ also can be fluorine or hydrogen when R′ is a $C_1$–$C_4$ alkyl group, a phenoxy group or a phenyl-$C_1$–$C_2$-alkoxy group.

7. A method according to claim 6 wherein $R_2'$ is a trifluoromethyl group, an acetyl group, an acetylamino group or an aminosulfonyl group with the proviso that $R_2'$ also can be fluorine or hydrogen in case R′ is a $C_1$–$C_4$-alkyl group, a phenoxy group or a phenyl-$C_1$–$C_2$-alkoxy group.

8. A method according to claim 6 wherein $R'_2$ is a trifluoromethyl group.

9. A method according to claim 6 wherein R′ is a $C_1$–$C_4$-alkoxy group or a phenoxy group and $R'_2$ is a trifluoromethyl group.

10. A method according to claim 6 wherein R′ is a $C_1$–$C_4$-alkyl group, a phenoxy group or a phenyl $C_1$–$C_2$-alkoxy group and $R'_2$ is hydrogen or flurorine.

11. A method according to claim 6 wherein R′ is a $C_1$–$C_4$ alkyl group, a phenoxy group, or a phenyl-$C_1$–$C_2$-alkoxy group.

* * * * *